United States Patent [19]

Kikuchi et al.

[11] Patent Number: 4,935,289
[45] Date of Patent: Jun. 19, 1990

[54] GAS SENSOR AND METHOD FOR PRODUCTION THEREOF

[75] Inventors: Toshimi Kikuchi, Yokohama; Masamichi Ippommatsu, Nishinomiya; Harutoshi Egami, Yokohama; Eikichi Ichimori, Tokyo; Tadashi Sakai, Yokohama, all of Japan

[73] Assignee: Kabushiki Kaisha Toshiba, Kanagawa, Japan

[21] Appl. No.: 260,759

[22] Filed: Oct. 21, 1988

[30] Foreign Application Priority Data

Sep. 18, 1986 [JP] Japan .................................. 61-220734
Oct. 22, 1987 [JP] Japan .................................. 62-267074

[51] Int. Cl.$^5$ ............................................. B32B 9/00
[52] U.S. Cl. .................................... 428/209; 428/210; 428/432; 428/433; 428/446; 428/457; 156/89; 427/58; 427/226; 427/261; 427/265; 427/282; 427/287
[58] Field of Search ................. 428/209, 210, 446, 457, 428/432, 433; 338/34; 156/89; 427/58, 96, 103, 226, 256, 258, 261, 265, 282, 287

[56] References Cited

U.S. PATENT DOCUMENTS 4,697,165 9/1987 Ishiguro et al. ..................... 338/34

FOREIGN PATENT DOCUMENTS 0064666 11/1982 European Pat. Off. .

Primary Examiner—Patrick Ryan
Attorney, Agent, or Firm—Finnegan, Henderson, Farabow, Garrett, and Dunner

[57] ABSTRACT

Disclosed is a gas sensor comprises a ceramic substrate, heaters formed on the surface of the substrate, an insulating layer formed as superposed on the heaters, electrodes formed on the surface of the insulating layer and a catalyst layer made of a gas detecting substance and formed as superposed on electrodes, and further disclosed is a method for the production of a gas sensor comprises the steps of forming a substrate of a ceramic substance, forming heaters on the surface of the substrate, forming an insulating layer for the substrate as superposed on the heaters, forming an electrode parts on the surface of the insulating layer and forming a catalyst layer made of a gas-detecting substance and superposed on the electrodes.

10 Claims, 4 Drawing Sheets

GAS SENSOR AND METHOD FOR PRODUCTION THEREOF

The present application is based on Japanese Patent Application No. 61-220734 filed on Sept. 18, 1986 and claims priority of Japanese Patent Application No. 62-267074 filed on Oct. 22, 1987.

FIELD OF THE INVENTION AND RELATED ART STATEMENT

This invention relates to a resistor type semiconductive gas sensor using a ceramic substrate and a method for the production thereof.

The semiconductive gas sensor is a device designed to detect passage of electric charge between a semiconductor and a gaseous molecule adsorbed on the semiconductor in the form of a change in conduction of electricity. It finds extensive utility as a sensor in a city gas alarm.

The semiconductive gas sensors which have been developed in recent years are those of the resistor type using a ceramic substrate. These gas sensors have a construction produced by forming, on one side (front surface) of the ceramic substrate, electrodes and a catalyst layer for contact with a gas and, on the other side (rear surface) thereof, a heater. When the leaking gas contacts the catalyst layer, the passage of electric charge consequently caused between the gaseous molecule and the catalyst layer induces a change in the electroconductivity, i.e. the magnitude of resistance, of the electrodes. The occurrence of gas leakage, therefore, is detected by the change to be produced in the magnitude of electric current flowing through the electrodes. The heater is caused by supply of electric current to generate heat and heat the catalyst layer. This heating is intended to heighten the sensitivity and response characteristic of the catalyst layer and, at the same time, deprive the catalyst layer of adhering dirt.

The semiconductive gas sensors of this construction have an advantage that they are advantageous in terms of manufacture and actual installation because they permit easy impartation of ample wall thickness and easy reduction in weight and volume. They nevertheless raise the following problems. The conventional gas sensors have electrodes and a catalyst layer on one surface of a ceramic substrate and a heater on the other surface thereof and, therefore, inevitably allow intervention of the ceramic substrate between the heater and the catalyst layer. Since the heat from the heater is conducted through the ceramic substrate to the catalyst layer, the degree of heat conduction is too low for the catalyst layer to be effectively heated. Further, the heater suffers from heavy loss of heat because the heater is formed in an exposed state on the surface of the ceramic substrate and, as the result, part of the heat from the heater is directly liberated into the ambient air instead of being utilized in heating the catalyst layer. There also arises a problem that the sensors suffer from deficiency in sensitivity and response characteristic unless the catalyst layer is effectively heated. In the manufacture of such a conventional gas sensor, a step of forming a heater by thick-layer printing and firing on one surface of a ceramic substrate, a step of forming a heater by thick-film printing and firing on the other surface of the ceramic substrate, and a step of forming electrodes by thick-film printing and firing on the other surface of the ceramic substrate are carried out independently of one another. In this connection, there arises another problem that the process of manufacture involves a large number of steps and the patterns to be deposited on the surfaces have weak strength of adhesion and the heater has no high reliability.

OBJECT AND SUMMARY OF THE INVENTION

This invention has been produced in the light of the true state of affairs of the prior art described above. An object of this invention is to provide a resistor type semiconductive gas sensor using a ceramic substrate, which gas sensor has sufficient sensitivity and excellent reliability and permit easy manufacture.

The first aspect of this invention concerns a gas sensor characterized by being provided with a ceramic substrate, heaters formed on the surface of the substrate, an insulating layer formed as superposed on the heaters, electrodes formed on the surface of the insulating layer, and a catalyst layer made of a gas-detecting substance and formed as superposed on the electrodes.

The catalyst layer of the gas sensor is made of a semiconductor possessing a gas sensitive characteristic and a catalyst serving to enhance the sensitivity in gas detection. The heat from the heater is conducted to the catalyst layer disposed on the same surface as the surface of the substrate on which the heater is disposed and the heat so conducted is utilized in efficiently heating the catalyst layer. Consequently, the sensor excels in sensitivity and response characteristic.

Further, since the heater is not exposed externally, the heat loss is small.

The conductor to be used for the heater is what is made mainly of a high melting metal (tungsten type). Among other tungsten type metals, the tungsten-platinum type alloy is particularly desirable because it excels in resistance to oxidation. Suitable, the platinum content of this alloy is in the range of 50 to 80% by weight.

By the first aspect of this invention, therefore, there is provided a resistor type semiconductive gas sensor using a ceramic substrate, which excels in sensitivity, enjoys highly satisfactory reliability, and permits easy production.

The second aspect of this invention concerns a method for the production of a gas sensor characterized by comprising a step of forming a substrate of a ceramic substance, a step of forming heaters on the surface of the substrate, a step of forming an insulating layer for the substrate as superposed on the heaters, a step of forming electrode parts on the surface of the insulating layer, and a step of forming a catalyst layer made of a gas detecting substance and formed as superposed on the electrodes.

The third aspect of this invention concerns a gas sensor characterized by being provided with a ceramic substrate, heaters formed on the surface of the substrate, an insulating layer formed as superposed on the heater, gas detecting layers formed on the surface of the insulating layer, a conductor layer formed on the rear surface of the substrate, and electrode parts connected to the heaters and the gas detecting layers.

The fourth aspect of this invention concerns a method for the production of a gas sensor, characterized by comprising a step of forming a substrate of a ceramic substance, a step of forming heaters on the surface of the substrate, a step of forming conductor layer on the rear surface of the substrate, a step of forming insulating layers on the obverse and reverse surfaces of the substrate as superposed on the heaters and the conductor layer, a step of forming electrode parts connected to the front surface of the insulating layer and the heaters, and a step of forming gas detecting layers on the surface of the insulating layer as superposed on the electrode parts.

DETAILED DESCRIPTION OF THE PREFERRED EMBODIMENT

Figure 1:
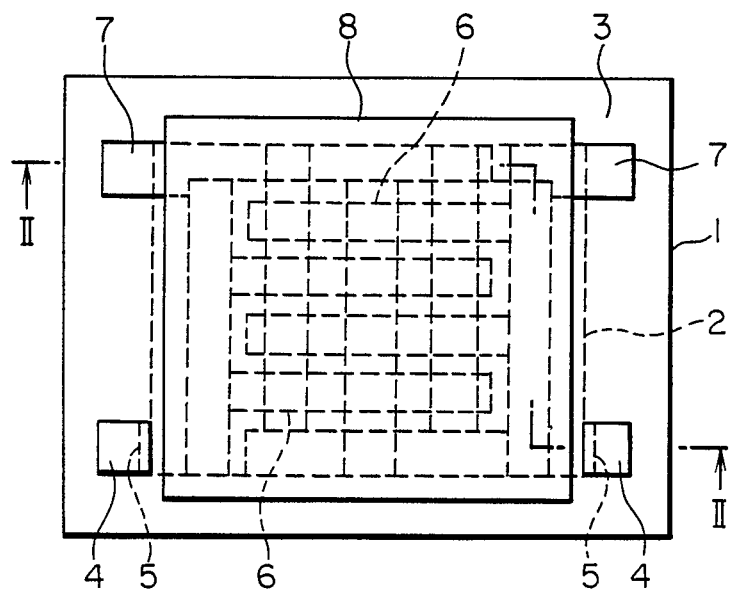
FIG. 1 is a plan view illustrating a typical gas sensor as one embodiment of this invention.

Now, this invention will be described more specifically below with reference to the accompanying drawings.

The construction of the gas sensor of this invention will be described with reference to FIG. 1 to FIG. 4.

In the drawings, reference numeral 1 stands for a rectangular substrate made of such a ceramic substance as alumina ($Al_2O_3$), for example. This substrate 1 has a thickness approximately in the range of 0.3 to 0.6 mm. Reference numeral 2 stands for each of the heaters made of a tungsten-platinum type alloy. The heaters 2 are formed as zigzagged throughout the entire area of one of the surfaces of the substrate 1. These heaters 2 have a thickness approximately in the range of 10 to 20 $\mu$m. Reference numeral 3 stands for an insulating layer made of such a ceramic substance as alumina, for example, similarly to the substrate 1. This insulating layer 3 is formed so as to cover the entire area of one of the surfaces of the substrate 1. The insulating layer 3 has a thickness approximately in the range of 40 to 60 $\mu$m. Reference numerals 4, 4 stand for heater terminals. These heater terminals 4, 4 are formed as dispersed in two corner portions of the front surface of the insulating layer 3 and are connected to the terminal parts of the heaters 2 via through holes bored in the insulating layer 3. The heater terminals 4, 4 have a thickness approximately in the range of 40 to 60 $\mu$m. Reference numerals 6, 6 stand for electrodes made of such an electrodic substance as platinum, for example. These electrodes 6, 6 each have a serrate shape and are formed in a combined pattern on the surface of the insulating layer 3. In the corner portions of the surface of the insulating layer 3 other than the pair of corner portions forming the heater terminals 4, 4, electrode terminals 7, 7 made of the same substance as the electrodes 6, 6 are formed. These electrode terminals 7, 7 are integrally connected to the electrodes 6, 6. The electrodes 6, 6 and the electrode terminals 7, 7 have a thickness approximately in the range of 3 to 6 $\mu$m. Reference numeral 8 stands for a catalyst layer. This catalyst layer 8 is formed on the surface of the insulating layer 3 as superposed on the electrodes 6, 6. The catalyst layer 8 is made of a gas sensitive substance or an oxide semiconductor such as, for example, $SnO_2$ highly sensitive to methane gas, $WO_3$ highly sensitive to carbon monoxide, or $LaNiO_3$ highly selective to an alcohol, depending on the particular use for which the sensor is intended. The catalyst layer 8 has a thickness approximately in the range of 1 to 4 $\mu$m.

The gas sensor constructed as described above is put to use by connecting the electrode terminals 7, 7 to a detection circuit to establish electric continuity from the electrode 6 through the catalyst layer 8 to the electrode and permit supply of electric current for signals. When a leaking gas contacts the catalyst layer 8, the magnitude of resistance of the catalyst layer 8 is changed to induce a corresponding change in the magnitude of electric current for the signal. Consequently, the detection circuit is enabled to detect the occurrence of gas leakage. Separately, the heater terminals 4, 4 are connected to a power circuit to advance flow of electric current to the heater 2 and cause the heater to generate heat. The heat from the heater 2 is conducted via the insulating layer 3 to the catalyst layer 8, enabling the catalyst layer 8 to be heated to a prescribed temperature. In this case, the insulating layer 3 has a thickness of about 40 to 60 $\mu$m, a value very small as compared with the thickness of the substrate 1. The conduction of heat from the heater 2 through the insulating layer 3 to the catalyst layer 8, therefore, is highly satisfactory as compared with the conduction of heat via the substrate 1. The catalyst layer 8, therefore, is heated effectively. Further, since the heaters 2 are enclosed with the substrate 1 and the insulating layer 3, the heat from the heaters 2 is not directly released into the ambient air but is utilized effectively in the heating of the catalyst layer 8. The heaters 2, therefore, are capable of amply heating the catalyst layer 8 and accomplishing ample enhancement of sensitivity and response characteristic of the sensor.

Now, the method for the production of the gas sensor constructed as described above will be described with reference to FIG. 5.

A green sheet 1 (denoted by the same reference numeral as used for the substrate for the sake of convenience) for substrate is obtained by applying ceramic powder to a surface by the well-known doctor blade process or the pressure molding process. On one surface of this green sheet 1, a heater 2 is formed by screen printing a paste as the raw material for the heater (FIG. 5 (a)). Then, an insulating layer 3 is formed on the surface of the green sheet 1 as superposed on the heater 2 (FIG. 5 (b)). In the insulating layer 3, through holes 5 are perforated. As means of forming the insulating layer 3, a method which comprises screen printing the paste as the raw material for the insulator layer on a surface and a method which directly attaches a green sheet of the same ceramic substance as the green sheet 1 fast to the surface of the green sheet 1 are available. Then, a paste as the raw material for the heaters is packed in the through hole 5 of the insulating layer 3 by screen printing and a paste as the raw material for the heater terminals is applied by screen printing on the surface of the insulating layer 3 to form the heater terminals 4, 4 (FIG. 5 (c)). Further, a paste as the raw material for the electrodes is applied by screen printing on the surface of the insulating layer 3 to form the electrodes 6, 6 and the electrode terminals 7, 7 (FIG. 5 (d)). The laminate produced as described above is fired in weakly reducing atmosphere at a temperature of 1,500° C. By this firing treatment, the laminate is fired in its entirety. Subsequently, a paste as the raw material for the gas detecting layer is applied by screen printing on the surface of the insulating layer 3 as superposed on the electrodes 6 to give rise to the catalyst layer 8. This catalyst layer 8 is fired at a temperature of 500° C., for example (FIG. 5 (e)). As a typical example of the paste for the catalyst layer, what is obtained by mixing tin octylate and niobium resinate at an atomic ratio of 1/100 and adding an organic solvent such as terpene oil and a binder to the resultant mixture is used.

By this method of manufacture, since the heaters 2 and the electrodes 6, 6 are formed by screen printing on the same surface of the substrate 1 and the substrate 1, the heaters 2, and the electrodres 6, 6 are fired at the same time, the number of steps of production process is smaller than the method which comprises forming heaters 2 and the electrodes 6, 6 on the different surfaces of the substrate 1 and firing them separately of each other. Further the patterns of these components are joined with sufficiently high adhesive strength to the surface, the heaters 2 consequently formed enjoy high reliability.

The method of manufacture has been described as carried out in the production of one gas sensor. A plurality of such gas sensors can be produced at one time. In this case, the multiplicity of gas sensors are simultaneously produced by performing the steps of process illustrated in FIG. 5 (a) to FIG. 5 (e) on a substrate sheet of a size equivalent to the total size of the plurality of substrates and then severing the sheet into separate portions.

The gas sensor of the preceding embodiment has been described as a monofunctional type having one species of catalyst layer formed on the substrate. Optionally, a plurality of catalyst layers made of different substances may be formed on one substrate to produce a gas sensor vested with as many gas detecting functions.

The gas sensor constructed as described above is excellent in sensitivity and reliability and is easy to produce.

Figure 7:
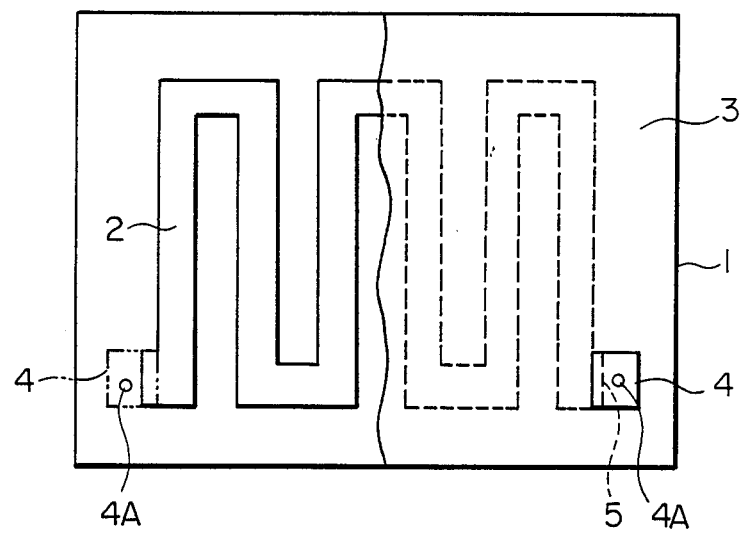
FIG. 7 is a plan view illustrating the heaters and the insulating layer on the obverse surface of the gas sensor illustrated in FIG. 5.
Figure 8:
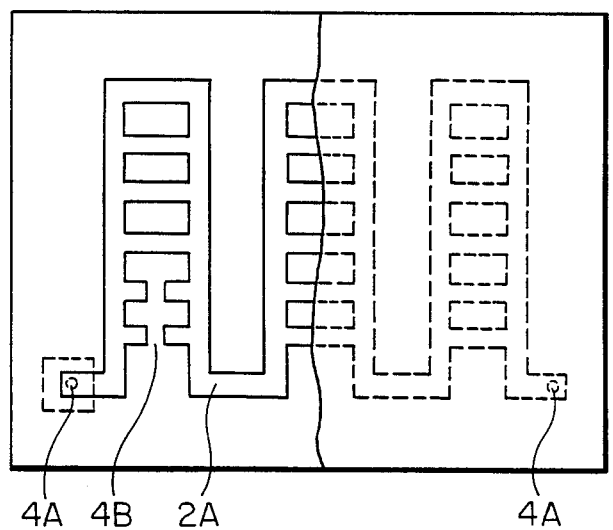
FIG. 8 is a plan view illustrating the heaters and the insulating layer on the reverse surface of the gas sensor illustrated in FIG. 5.

Now, the gas sensor of another construction contemplated by the present invention will be described below with reference to FIG. 6 to FIG. 8.

Figure 2:
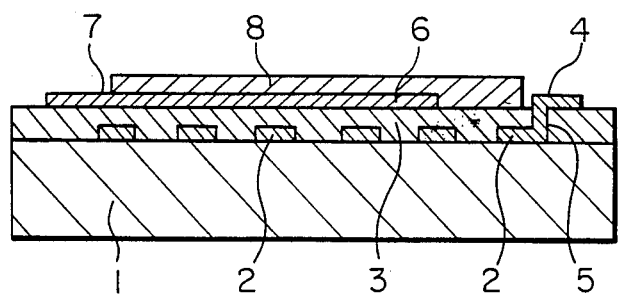
FIG. 2 is a cross section taken through FIG. 1 across the line II—II.
Figure 3:
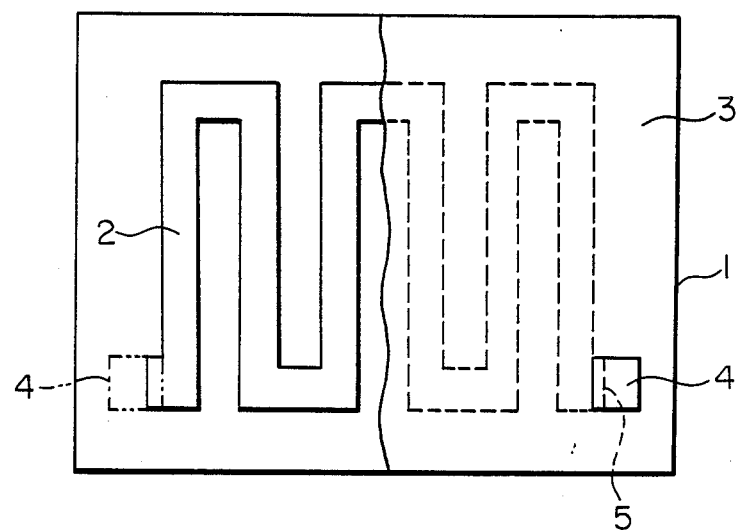
FIG. 3 is a plan view illustrating heaters and illustrating electrodes and a catalyst layer of the gas sensor.
Figure 4:
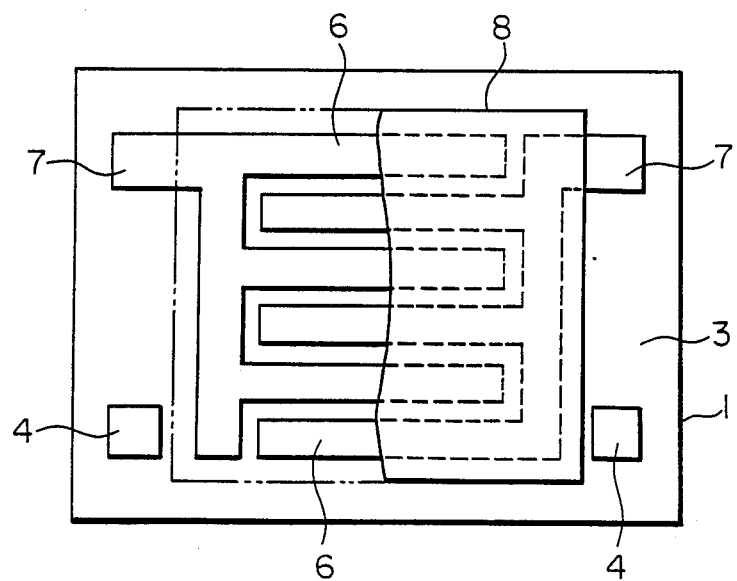
FIG. 4 is a plan view illustrating electrodes and a catalyst layer of the gas sensor.
Figure 5A:
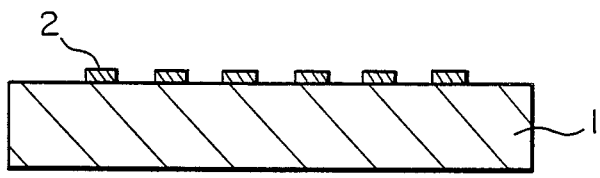
FIG. 5 (a) to (e) are cross sections illustrating a process for the production of a gas sensor.
Figure 5B:
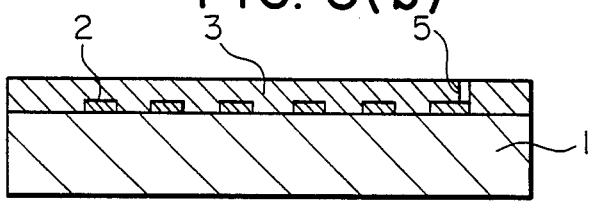
Figure 5C:
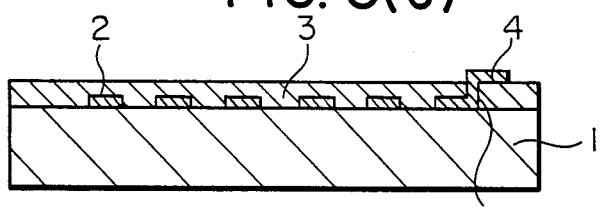
Figure 5D:
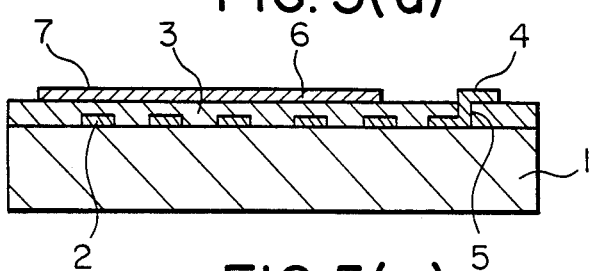
Figure 5E:
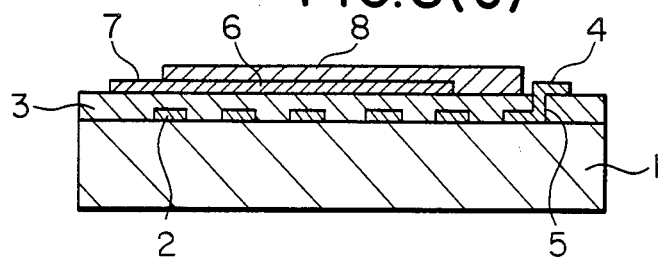
Figure 6:
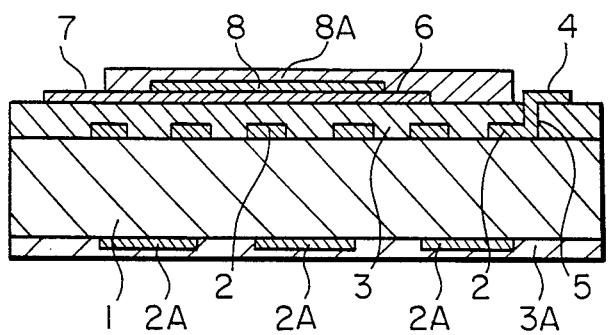
FIG. 6 is a cross section of another typical gas sensor.

On FIG. 6, the component parts of equal function to those of FIG. 2 will be denoted by equal reference numerals. The gas sensor illustrated in FIG. 6 is characterized by having heaters which form a conductor layer 2A and an insulating layer 3A formed on the reverse surface of the substrate 1.

Reference numerals 2, 2A stand for heaters made of a tungusten-platinum alloy, for example. The heaters 2 are formed as zigzagged throughout the entire area of the observed surface of the substrate as illustrated in FIG. 7. The heaters 2, 2A are interconnected via through holes 5 bored in the substrate at the heater terminals 4. The heaters 2A formed on the reverse surface are shaped like a lattice as illustrated in FIG. 8. The route for connection of electricity in the heaters may be altered by inserting cuts therein as by the use of a laser beam (4B, for example). The magnitude of resistance of the heaters may be adjusted by this modification.

Reference numeral 3A stands for an insulating layer which serves the purpose of covering the heaters 2A on the reverse side of the ceramic substrate. The insulating layer 3A has a thickness approximately in the range of 10 to 20 $\mu$m. Reference numerals 8, 8A stand for gas detecting layers. These gas detecting layers 8, 8A are formed on the surface of the insulating layer 3 as superposed on the electrodes 6, 6. The gas detecting layer 8 is made of a gas sensitive substrate or an oxide semiconductor such as $SnO_2$ highly sensitive to methane gas, $WO_3$ highly sensitive to carbon monoxide, or $LaNiO_3$ highly selective to alcohol, depending on the particular use for which the sensor is intended. Optionally, it may be made of a combination of different species of oxide semiconductors. This layer has a thickness of not more than 5 $\mu$. The catalyst layer 8A is intended to enhance the gas detecting sensitive and is formed as superposed on the layer of an oxide semiconductor.

This gas sensor is capable of adjusting the resistance of the heaters by means of the heaters formed on the reverse surface of the ceramic substrate as described above. Thus, the heating of the gas detecting layers 8, 8A can be carried out more uniformly. The gas sensor which is produced with adjusted heater resistance possesses a magnitude of resistance within the range of ±5% of the specified magnitude of heater resistance, indicating an improvement in accuracy as compared with the gas sensor of unadjusted heater resistance which suffers from a deviation of as much as ±8% to 10%.

In the gas sensor of this construction, since the heaters effectively heat the gas detecting layer and improve sensitivity and response characteristic and the heaters are adapted to generate a uniform magnitude of resistance, the sensor is enabled to manifest a highly reliable gas detecting characteristic.

The method for the production of the gas sensor constructed as described above will be explained below with reference to FIG. 6. A green sheet 1 (denoted by the same reference numeral as that of the substrate for the sake of convenience) for the substrate is obtained by shaping a ceramic powder by the pressure molding method or the doctor blade method. The heaters 2, 2A are formed by applying a paste as the raw material for the heaters by screen printing on the obverse and reverse surface of the green sheet 1. Then, the insulating layers 3, 3A are formed on the surface of the green sheet 1 as superposed on the heaters 2, 2A. In the insulating layer 3, the through hole 5 is formed. As means of forming the insulating layers 3, 3A, a method which comprises applying the paste for the insulating layer on a given surface by screen printing and a method which comprises joining a green sheet of the ceramic substrate as the green sheet 1 fast to the green sheet 1 by thermocompression bonding are available. Then, the paste as the raw material for the heaters is packed by screen printing in the through hole 5 of the insulating layer 3 and the heater terminals 4, 4 are formed by applying the paste as the raw material for the heater terminals by screen printing to the surface of the insulating layer 3. The terminals 4 are connected to the heaters 2A on the reverse surface via the through hole 4A. Further, the electrodes 6, 6 and the electrode terminals 7, 7 are formed by screen printing the paste as the raw material for the electrodes on the surface of the insulating layer 3. The laminate produced consequently is fired in a weakly reducing atmosphere at a temperature of 1,500° C., for example. By this firing treatment, the laminate is fired in its entirety. Subsequently, the gas detecting layer 8 is formed by screen printing the paste as the raw material for the gas detecting layer on the surface of the insulating layer 3 as superposed on the electrodes 6.

This detecting layer 8 is fired at a temperature of 500° C., for example.

What is claimed is:

1. A semiconductive gas sensor comprising:
   a ceramic substrate;
   a heater layer formed on said substrate, said heater layer consisting essentially of a tungsten alloy;
   an insulating layer formed on said heater layer, said insulating layer having a thickness of not more than 60 μm;
   an electrode formed in a combined pattern on said insulating layer; and
   at least one layer of an oxide semiconductor catalyst formed on said electrode.

2. The semiconductive gas sensor according to claim 1, wherein said tungsten alloy is a tungsten-platinum alloy.

3. A method for the production of a semiconductive gas sensor, comprising the steps of:
   (a) forming a green sheet consisting essentially of a ceramic powder;
   (b) applying a paste consisting essentially of a tungsten alloy on said green sheet by screen printing to form a heater pattern;
   (c) applying an insulating ceramic paste on said heater pattern by screen printing to form an insulating layer having a thickness not more than 60 μm;
   (d) applying a conductive paste on said insulating layer to form a combined pattern electrode;
   (e) firing the resultant laminate obtained by steps (a) to (d) in a reducing atmosphere at a temperature of about 1500° C.; and
   (f) applying a catalyst paste consisting essentially of an oxide semiconductor on said fired laminate by screen printing and firing said catalyst paste thereon at a temperature of about 500° C.

4. The method according to claim 3, wherein said tungsten alloy is a tungsten-platinum alloy.

5. A semiconductive gas sensor comprising:
   a ceramic substrate;
   a heater layer formed on one surface of said substrate, said heater layer consisting essentially of a tungsten alloy;
   an insulating layer formed on said heater layer, said insulating layer having a thickness of not more than 60 μm;
   an electrode formed in a combined pattern on said insulating layer;
   at least one layer of an oxide semiconductor catalyst on said electrode; and
   a conductor layer formed on the rear surface of said substrate.

6. The semiconductive gas sensor according to claim 5, wherein said conductor layer formed on the rear surface of the substrate is a heater layer adapted to form electric continuity with the heater layer formed on said one surface of said substrate.

7. The semiconductive gas sensor according to claim 5 or claim 6, wherein said heater layer and said conductor layer consist essentially of a tungsten-platinum alloy.

8. A method for the production of a semiconductive gas sensor, comprising the steps of:
   (a) forming a green sheet consisting essentially of a ceramic powder;
   (b) applying a paste consisting essentially of a tungsten alloy on one surface of said green sheet by screen printing to form a heater pattern;
   (c) applying an insulating ceramic paste on said heater pattern by screen printing to form an insulating layer having a thickness not more than 60 μm;
   (d) applying a conductive paste on said insulating layer to form a combined pattern electrode;
   (e) applying a paste consisting essentially of a tungsten alloy on the rear surface of said green sheet to form a conductor layer;
   (f) applying an insulating ceramic paste on said conductor layer;
   (g) firing the resultant laminate obtained by steps (a) to (f) in a reducing atmosphere at a temperature of about 1500° C.; and
   (h) applying a catalyst paste consisting essentially of an oxide semiconductor on said fired laminate, and firing said catalyst paste thereon at a temperature of about 500° C.

9. The method according to claim 8, wherein said conductor layer formed on the rear surface of the green sheet is a heater layer adapted to form electric continuity with the heater layer formed on said one surface of said green sheet.

10. The method according to claim 8 or claim 9, wherein said heater layer and said conductor layer consist essentially of a tungsten-platinum alloy.

* * * * *